United States Patent [19]

Lutz

[11] 4,011,309

[45] Mar. 8, 1977

[54] DENTIFRICE COMPOSITION AND METHOD FOR DESENSITIZING SENSITIVE TEETH

[75] Inventor: Herman J. Lutz, Hatboro, Pa.

[73] Assignee: Marion Laboratories, Inc., Kansas City, Mo.

[22] Filed: Jan. 14, 1976

[21] Appl. No.: 648,977

Related U.S. Application Data

[63] Continuation-in-part of Ser. No. 542,520, Jan. 20, 1975, abandoned.

[52] U.S. Cl. .............................................. 424/49
[51] Int. Cl.² ........................................ A61K 7/16
[58] Field of Search .................................... 424/49

[56] References Cited

UNITED STATES PATENTS 3,876,759   4/1975   Pensak et al. ..................... 424/58

FOREIGN PATENTS OR APPLICATIONS 162,082   8/1953   Australia ............................ 424/50

*Primary Examiner*—Shep K. Rose
*Attorney, Agent, or Firm*—Howson and Howson

[57] ABSTRACT

A dentifrice composition and method for desensitizing teeth is disclosed. The dentifrice composition is an aqueous gel comprising citric acid, sodium citrate, a non-ionic surfactant which is the condensation product of a normally-solid, water-soluble, high molecular weight condensation product of ethylene oxide and polypropylene glycol and containing about 70% polyoxyethylene, and water. The dentifrice composition can be topically applied to sensitive teeth to desensitize them.

4 Claims, No Drawings

DENTIFRICE COMPOSITION AND METHOD FOR DESENSITIZING SENSITIVE TEETH

This application is a continuation-in-part of application Ser. No. 542,520, filed Jan. 20, 1975, now abandoned.

BACKGROUND OF THE INVENTION

Cementum and dentin hypersensitivity is one of the most painful, ubiquitous, and least satisfactorily treated of chronic oral problems involving teeth. Painful reactions are commonly elicited by thermal, mechanical, and chemical stimuli which are transmitted to the pulp. To date, the precise mechanism for dentin sensitivity has not been established. However, hyperesthetic areas are easily identified; careful examination of these sites reveals that either the enamel or the cementum or both, have eroded or planed away leaving dentin exposed.

Home treatment is required as an adjunct to chairside therapy for hypersensitivity, as such therapy provides only temporary relief. Moreover, exposed root surfaces which are not kept clean may become increasingly hypersensitive. Because of the discomfort associated with brushing these areas, the patient tends to avoid them in his normal oral hygiene regimen. Without effective home care, any relief obtained in the dental office is likely to be transitory. Traditionally, home treatment has included a variety of medicaments which are intended to occlude or cover the lumina of the dentinal tubules.

A number of desensitizing formulations have been attempted with varying degrees of success and duration of effectiveness. One of the earlier dentifrices was a formalin-containing paste. Others have included zinc chloride, silver nitrate, glycerin, strontium chloride, and the fluorides, the latter two being of particular interest. The desensitizing effect of strontium chloride has been investigated for over a decade and is available commercially in a dentifrice. As early as 1943, the use of sodium fluoride for desensitizing dentin was reported. More recently, the effectiveness of stannous fluoride in an anhydrous glycerin gel has been demonstrated.

OBJECTS OF THE INVENTION

A primary object of this invention is to provide a novel dentifrice composition in the form of an aqueous gel which is effective to reduce significantly the sensitivity of sensitive teeth to external factors, which composition can be readily applied to sensitive teeth.

Another object of this invention is the provision of a dentifrice composition in the form of an aqueous gel intended for topical application to sensitive teeth comprising comparatively inexpensive and readily available constituents, namely citric acid, sodium citrate, certain non-ionic polyol surfactants and water.

A further object of this invention is to provide a method for desensitizing sensitive teeth by simple topical application of the novel desensitizing dentifrice to sensitive teeth.

These and other objects of the invention will become apparent from the following detailed description of the invention.

DETAILED DESCRIPTION OF THE INVENTION

The novel tooth desensitizing dentifrice composition of this invention is in the form of an aqueous gel and comprises four essential constituents, namely citric acid, sodium citrate, a particular water-soluble, non-ionic polyol surfactant, and water. A particularly preferred composition comprises about 0.5 percent citric acid, about 1.5 percent sodium citrate, about 22 percent of non-ionic polyol surfactant and water. The foregoing percentage are by weight based on the total weight of the dentifrice composition.

It is believed that the effectiveness of the dentifrice composition of this invention is attributed to the following mechanism. However, there is no intention to be bound by such theory, or to limit the scope of the claims to such mechanism. Rather, the theory as to the effeciency of the formulation is advanced merely for the purpose of a possible explanation.

It appears that the citrate anion which is present in the dentifrice composition of this invention forms a non-ionized complex with the calcium cation of the vast surface of bone crystal exposed in the dental tubules and tooth surface. Apparently the calcium citrate complex acts as a protectant, or occluding agent. The polyol surfactant, which is essentially tasteless, is the gelforming component which imparts physical stability, controlled foaming, excellent rinsability and stain-removing properties. In addition, the polyol, when present in a gel-forming amount, apparently enhances the effectiveness of the citrate anion as a desensitizing agent by facilitating penetration of the citrate ion into the tooth surface.

As indicated above, in the dentifrice of this invention there is used in combination citric acid and sodium citrate. These two essential constitutents, together with the polyol surfactant, produce the unexpected advantageous results of effectively desensitizing teeth as can be determined by reference to the specific examples and test results described hereinbelow.

The citric acid may comprise from about 0.1 to about 3 percent, preferably from about 0.2 to about 1 percent of the dentifrice. As noted previously, a particularly preferred amount is about 0.5 percent.

Sodium citrate has the formula $C_6H_5Na_3O_7 \cdot 2H_2O$, and should be present in the dentifrice in an amount between about 0.3 and about 9 percent, by weight. Preferably, the citrate comprises from about 0.6 to about 3 percent, by weight of the product, more preferably about 1.5 percent.

When the citric acid and citrate are present in these amounts, the dentifrice will have a pH of from about 5 to about 6.5. The preferred pH of the dentifrice is about 5.2 to 6.2.

The third essential constituent of the tooth desensitizing composition is a normally-solid, substantially water-soluble, nonionic polyol surfactant which is a condensation product of ethylene oxide and polypropylene glycol. These condensation products are prepared by the controlled addition of propylene oxide to the two hydroxyl groups of a propylene glycol nucleus. The resulting hydrophobe can be tailored to any desired length and in the polyol employed in the instant dentifrice, the poly (oxypropylene) hydrophobe portion should have a molecular weight of from about 950 to about 4000. Ethylene oxide is then reacted with the hydrophobe whereby the hydrophobe base is sandwiched in between hydrophilic poly (oxyethylene) groups which are controlled so that the final block polymer comprises from about 65 percent to about 80 percent, by weight of polyoxyethylene. The final polyols may be represented by the formula:

wherein $(C_3H_6O)_b$ is a poly (oxypropylene) glycol residue of a sufficient number of mols (b) or molecular weight (at least 950) to render the same water-insoluble or hydrophobic, and (a) + (c) represent the number of mols of ethylene oxide condensed therewith to render the condensation product normally-solid and water-soluble (about 65 yo 80 percent by weight polyoxyethylene).

The condensation products may be prepared by well known methods such as those described in U.S. Pat. Nos. 2,773,801 and 3,740,421.

It is preferred to use such condensation products having a total molecular weight within the range of about 8,000 to about 14,000, preferably about 12,500. A preferred commercially available polyol which has provided excellent results is sold under the trade name "Pluronic F-127." The total average molecular weight of this polyol is about 12,500, and the molecular weight of the poly (oxypropylene) hydrophobe is about 4000. The polyol comprises about 70 percent, by weight of polyoxyethylene, is water-soluble, normally-solid, and has a melting point of 56° C.

The polyol may comprise from about 19 to about 25 percent, by weight, of the dentifrice composition. When present in this amount, the product is in the form of an aqueous gel, i.e., an open filament like structure formed of minute colloidal particles joined together. The gel structure is capable of absorbing large amounts of water similar to that of a sponge.

The fourth essential constituent is water, preferably deionized water, in order to prevent precipitation of the citrate anion in the form of a substantially water-insoluble salt. The water provides the remainder of the composition, i.e. a quantity sufficient to provide 100 percent.

In addition to the essential constituents above described, the novel dentifrice compositions of this invention may contain certain additional ingredients. Thus, although the surfactant polyol imparts stain-removing properties to the composition, the compositions may also contain additional detergent or cleaning agents. The particular detergent and the amount thereof may be the same as employed in conventional dentifrice preparations. Suitable materials include soaps, i.e., water soluble salts of higher fatty acids, as well as synthetic detergents.

Any suitable practically water-insoluble polishing agent may be included in the dentifrice composition. There is a relatively large number of such materials known in the dental art. Representative materials include, for example, calcium carbonate, dicalcium phosphate (anhydrous or hydrated), sodium metaphosphate, aluminum hydroxide, magnesium carbonate, etc. Such polishing agents may comprise up to about 60 percent, by weight of the composition.

Flavoring materials may be used to impart a pleasant taste to the composition and to make the same more palatable. Suitable flavoring materials include oil of peppermint, oil of wintergreen, oil of spearmint, oil of eucalyptus, cloves, methol, amise, thyme, etc.

The novel dentifrice composition of this invention may be prepared by either the hot or cold technique, preferably the latter. In the hot technique, deionized water is placed in a suitable vessel and the citric acid, sodium citrate, flavoring etc., are added followed by the addition of the polyol surfactant, with gentle, but thorough stirring. The temperature of the mixture is raised to about 80° C. with gentle stirring until the system is homogeneous. The mixture is then transferred to suitable containers and upon cooling to room temperature the product gels.

In the cold technique the surfactant polyol is dissolved along with the other ingredients, in deionized water at a temperature with the range of 5–10° C. When solution is complete, the system is brought to room temperature, whereupon it forms a gel. Water-insoluble ingredients, if any, may be incorporated by combining them with the polyol at elevated temperatures to melt the polyol, followed by slow addition of cold water to the molten mixture to bring the temperature below that at which gelation takes place.

The dentifrice composition of this invention can be used in regular daily brushing in the same manner as ordinary well known commercial toothpastes. It can be applied topically in any of a number of ways as recommended by a person's dentist.

EXAMPLES OF USE OF DENTIFRICE

EXAMPLE 1

A desensitizing dentifrice composition according to the invention was prepared by the "cold" method in which the several constituents listed in Table I, below, were dissolved in water at 5°–10° C. When solution was complete, the system was brought to room temperature, whereupon it formed a ringing gel.

Table I

| Constituent | Weight Percent |
| --- | --- |
| Coloring Agent | 0.0006 |
| Citric Acid | 0.500 |
| Sodium Citrate | 1.500 |
| Glycerin | 8.800 |
| Water Insol. Polishing Agents | 4.0 |
| Pluronic F127 | 22.000 |
| Flavor | 0.700 |
| Deionized Water | q.s. to 100.000 |

EXAMPLE 2

A dentifrice composition similar to that of Example 1, but containing additional deionized water in place of citric acid and sodium citrate was prepared in the same manner as the dentifrice of Example.

EXAMPLE 3

A dentifrice (typical toothpaste formula) containing 10 percent, by weight of strontium chloride, a known tooth desensitizer, was prepared and had the composition set forth in Table II below.

Table II

| Constituent | Weight Percent |
| --- | --- |
| Strontium chloride 6 H$_2$O | 10.0[1] |
| Water | 36.2 |
| Glycerin | 25.0 |
| Hydroxyethylcellulose | 1.6 |
| Polyoxyethylene sorbitan monolaurate | 2.0 |
| Micronized silica | 24.0 |
| Spearmint oil | 1.0 |
| Saccharin | 0.2 |

[1]Equivalent to 3.3% strontium ion concentration.

EXAMPLE 4

A composition for dental-application was prepared by dissolving 0.4 percent, by weight of Stannous fluoride in substantially anhydrous glycerol.

EXAMPLE 5

A Control Composition was prepared having the formulation given in Table III.

Table III

| Constituent | Weight Percent |
| --- | --- |
| Silica xerogel | 14.0 |
| Silica aerogel | 7.5 |
| Sodium carboxymethylcellulose | 0.6 |
| Saccharin | 0.2 |
| Sorbitol | 47.0 |
| Sodium benzoate | 0.08 |
| 1% dye solution | 0.5 |
| Flavoring agent | 1.0 |
| Chloroform | 0.8 |
| Sodium lauryl sulfate/glycerin mixture | 7.0 |
| Water | q.s. to 100.00 |

Samples of the dentifrice compositions of Examples 1 to 5, inclusive, were used to treat a number of patients with hypersensitive teeth in order to evaluate the efficacy of the novel product of this invention.

Subjects for the study were drawn from a general adult population in the vicinity of a sub-regional hospital in Puerto Rico. The study was conducted in the dental clinic of that hospital. The subjects were selected on the basis of a clinical examination which evaluated the presence and extent of tooth hypersensitivity. The criteria for subject selection were as follows:

1. Cervical hypersensitivity to thermal or mechanical stimuli
2. No history of treatment for hypersensitivity for at least three months
3. Willingness to participate
4. No active cervical caries
5. No hypersensitivity due to occlusal trauma
6. No essential dental treatment during the examination period Of over 400 potential subjects initially screned, 176 ranging in age from 18 to 63 years were ultimately selected as participants.

The subjects received a thorough clinical examination during which the precise location and number of hypersensitive tooth surfaces were recorded. This was determined by a light stroke of a dental explorer along the cervical areas of all teeth present.

This procedure is quite accurate and reproducible, and almost without fail, a subject's response to the painful stimulus was accompanied by a closing of eyelids reaction. This phenomenon always precedes the subject's verbal expression of pain and can be used as a diagnostic criterion for hypersensitivity. Using this technique, the dental examiner can return to a precise location in future examinations and can determine whether or not that particular surface is still sensitive.

Dental explorers were used approximately five times in screening examinations, then discarded. The examiner at all times applied the same degree of pressure when probing the cervical areas. Subsequent examinations were conducted in an identical manner by the same examiner.

The subjects were randomly assigned to five balanced groups of approximately 35 members each. The dentifrices assigned to each group were as follows:

Group I - 10% strontium chloride in a typical toothpaste formula (Example 3).

Group II - 0.4% stannous fluoride in anhydrous glycerol (Example 4)

Group III - 0.5% citric acid and 1.5% sodium citrate (Example 1)

Group IV - Polyol formula (Example 2)

Group V - a control dentifrice (Example 5)

The subjects were given no specific instructions regarding method or frequency of toothbrushing; thus, they continued to brush in their normal manner.

The study was conducted doubleblind. The dentifrices in coded packages and toothbrushes were issued at the initial examination. At no time were the examiner or the subjects aware of the contents of the packages. A doubleblind study is mandatory in assessing the effectiveness of desensitizing agents in view of the variables which influence the evaluation of treatment.

The subjects were examined for hypersensitivity three times during the six weeks of the study:

1. The initial examination. At this time, the number and location of hypersensitive surfaces were determined.
2. One week later, at which time the original surfaces were again scored for the presence or absence of hypersensitivity.
3. Six weeks later, at which time the original surfaces were again scored for the presence or absence of hypersensitivity.

For statistical accuracy, scores for all surfaces were recorded in absolute terms: an originally sensitive surface was noted as being still sensitive or not sensitive.

RESULTS

An examination of the scores from the initial examination indicated a relatively well-balanced distribution of hypersensitive surfaces. Approximately ⅔ (61%–67%) of all patients in each group had two or three sensitive tooth surfaces at the beginning of the study.

Scores recorded at the first week examination disclosed at least a 50% reduction in the number of sensitive surfaces within all groups. Discrimination between groups was not possible because of the high initial response.

Additional improvement was noted at the end of six weeks. At this time it was possible to differentiate individual responses to the desensitizing effects of the various dentifrices. The results are tabulated in Table IV, below:

Table IV

| Treatment Group | Number of Sensitive Surfaces | | % Improvement |
| --- | --- | --- | --- |
| | Baseline | Six Weeks | |
| I | 85 | 23 | 72.9 |
| II | 111 | 32 | 71.2 |
| III | 98 | 16 | 83.7 |
| IV | 102 | 27 | 73.5 |
| V | 90 | 36 | 60.0 |

Partitioning the above results in two-way contingency tables makes it possible to compare the various treatment combinations. Comparisons were made using the Fisher's Exact Test which provides the probability that the observed distribution could have occurred. Table illustrates the conclusion of a comparison of all active treatment groups to the control with respect to reduction in the number of sensitive surfaces. The number of sensitive surfaces of those subjects in Group III (dentifrice of this invention) was significantly lower ($p<.001$) than those observed in the control group.

Table V

| Comparison | Outcome | Level of Significance |
|---|---|---|
| 1. Group I vs. Group V | Marginal | $p = .07$ |
| 2. Group II vs. Group V | Not Significant | $p < .10$ |
| 3. Group III vs. Group V | Significant Difference | $p < .001$ |
| 4. Group IV vs. Group V | Significant Difference | $p < .05$ |

Further significance was indicated when the Group III dentifrice (present invention) was compared to the other active treatments. A significant difference ($p<.05$) was found between the Group III dentifrice and the Group II dentifrice (stannous fluoride) in the reduction of sensitive surfaces after six weeks. Also, the difference between Group III and Group I (strontium chloride) was found to be marginally significant in the same context as above ($p=.06$).

A comparison of dentifrices by number of asymptomatic subjects at six weeks revealed that Group III (present invention) had a significantly ($p<.05$) greater proportion of asymptomatic patients than the control group.

Table VI

| Treatment Group | Asymptomatic Patients at Six Weeks | | |
|---|---|---|---|
| | Number Asympotmatic | Number Examined | Percent |
| I | 21 | 33 | 63.6 |
| II | 23 | 34 | 67.6 |
| III | 25 | 33 | 75.8 |
| IV | 22 | 34 | 64.7 |
| V | 17 | 34 | 50.0 |

As noted earlier, the results of chairside treatment with chemotherapeutic agents and clinical procedures have been generally transitory. Supplemental home treatment is required to decrease or eliminate hypersensitivity to any appreciable degree. A number of theories have been advanced to explain the mechanism whereby painful stimuli are transmitted from the exposed dentin.

1. Innervation of the dentinal tubules, permitting transmission of impulses to the pulp.
2. The presence of lymph fluid in the dentinal tubules. Exposure of dentin results in increased colloidal pressure on the tubules, thereby increasing pressure on the odontoblastic cells.
3. A hydrodynamic mechanism involving the movement of tubular fluid in either direction, which stimulates the pulpal nerve.

Despite the controversy which surrounds the exact mechanism of transmission, occlusion of the dentinal tubules is definitely indicated. The effectiveness of the Group III mechanism (dentifrice of present invention) can be seen as a result of such occlusion. The citrate anion of this formulation is believed to form a non-ionized complex with the calcium cation of the bone crystal surface in the dentinal tubules and tooth surface. This calcium citrate complex acts as a protectant, or occluding agent.

The gelation agent, a polyol surfactant, which is a water-soluble condensation product of ethylene oxide and polypropylene glycol, provides excellent wetting, detergency, and stability. Apparently the polyol itself possesses a marked ability to cleanse tooth surfaces (Group IV, Example 2). These wetting and detergency properties enhance the effectiveness of the citrate ion as a desensitizing agent by facilitating the penetration of the citrate anion into the tooth structure.

In addition, the statistically significant effect of the formulation in Group IV (Example 2), implies that the polyol itself has a desensitizing ability.

The above-discussed tests show that the novel dentifrice of this invention has significant effectiveness ($p<.001$) in the reduction of cementum and dentin hypersensitivity. It is believed that the novel product has better occluding properties and a longer duration of effect than formulations presently available. In addition, the new dentifrice advantageously does not unduly irritate the pulp, is relatively painless when applied, can be readily applied using standard dental techniques, acts rapidly, is relatively permanently effective, and does not discolor the tooth.

Although the present invention has been described with reference to particular embodiments and examples, it will be apparent to those skilled in the art that variations and modifications of this invention can be made and that equivalents can be substituted therefor without departing from the principles and true spirit of the invention.

What is claimed is:

1. A tooth desensitizing dentifrice composition in the form of an aqueous gel comprising from about 0.1 to about 3 percent by weight of citric acid, from about 0.3 to about 9 percent of sodium citrate, from about 19 to about 25 percent of a normally-solid, water-soluble condensation product of ethylene oxide and polypropylene glycol, said condensation product having a molecular weight of about 8,000 to about 14,000, and a polyoxyethylene content of from about 65 to about 80 percent by weight, and water.

2. The tooth desensitizing dentifrice composition of Claim 1 comprising about 0.5 percent citric acid, about 1.5 percent sodium citrate, about 22 percent of said condensation product of ethylene oxide and polypropylene glycol, said condensation product havng an average molecular weight of about 12,500 and a polyoxyethylene content of about 70 percent by weight, and water.

3. The method of desensitizing sensitive teeth comprising topically applying to teeth a tooth desensitizing dentifrice composition which is an aqueous gel comprising from about 0.1 to about 3 percent by weight of citric acid, from about 0.3 to about 9 percent of sodium citrate, from about 19 to about 25 percent of a normally-solid, water-soluble condensation product of ethylene oxide and polypropylene glycol, said condensation product having a molecular weight of about 8,000 to about 14,000, and a polyoxyethylene content of from about 65 to about 80 percent by weight, and water.

4. The method of desensitizing sensitive teeth according to claim 3 in which said tooth desensitizing composition comprises about 0.5 percent citric acid, about 1.5 percent sodium citrate, about 22 percent of said condensation product of ethylene oxide and polypropylene glycol, said condensation product having an average molecular weight of about 12,500 and a polyoxyethylene content of about 70 percent by weight, and water.

* * * * *